(12) United States Patent
Lee et al.

(10) Patent No.: US 11,311,256 B2
(45) Date of Patent: Apr. 26, 2022

(54) MOBILE X-RAY IMAGING APPARATUS

(71) Applicant: SAMSUNG ELECTRONICS CO., LTD., Suwon-si (KR)

(72) Inventors: Jin-woo Lee, Suwon-si (KR); Dae-woong Han, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/445,750

(22) Filed: Jun. 19, 2019

(65) Prior Publication Data

US 2019/0298284 A1 Oct. 3, 2019

Related U.S. Application Data

(63) Continuation of application No. 15/627,655, filed on Jun. 20, 2017, now Pat. No. 10,335,102.

(30) Foreign Application Priority Data

Oct. 20, 2016 (KR) .................. 10-2016-0136249
Jan. 16, 2017 (KR) .................. 10-2017-0007031

(51) Int. Cl.
*A61B 6/00* (2006.01)
*A61B 6/10* (2006.01)

(52) U.S. Cl.
CPC .......... *A61B 6/4405* (2013.01); *A61B 6/102* (2013.01); *A61B 6/4452* (2013.01); *A61B 6/4458* (2013.01); *A61B 6/46* (2013.01); *A61B 6/465* (2013.01); *A61B 6/54* (2013.01); *A61B 6/547* (2013.01); *A61B 6/4482* (2013.01)

(58) Field of Classification Search
None
See application file for complete search history.

(56) References Cited

U.S. PATENT DOCUMENTS

| 4,178,508 A | 12/1979 | Hotta et al. |
| 6,206,566 B1 | 3/2001 | Schuetz |
| 8,672,543 B2 | 3/2014 | Kralles et al. |
| 8,781,073 B2 * | 7/2014 | Kim .................. A61B 6/46 378/98 |
| 8,953,742 B2 * | 2/2015 | Yoshida ............ A61B 6/4233 378/114 |

(Continued)

FOREIGN PATENT DOCUMENTS

| EP | 2859849 A1 | 4/2015 |
| JP | 2013-523400 A | 6/2013 |

(Continued)

OTHER PUBLICATIONS

Communication dated May 2, 2018, issued by the Korean Intellectual Property Office in corresponding Korean Application No. 10-2017-0007031.

(Continued)

*Primary Examiner* — Hoon K Song
(74) *Attorney, Agent, or Firm* — Sughrue Mion, PLLC

(57) ABSTRACT

A mobile X-ray imaging apparatus includes a first column rotatably coupled to a main body and extending in one direction; a second column extending in the one direction and slidably coupled to the first column in an extension direction of the first column; a display provided in the main body; and a indicator arranged in one end of the second column.

19 Claims, 13 Drawing Sheets

(56) References Cited

U.S. PATENT DOCUMENTS

| | | | |
|---|---|---|---|
| 8,961,011 | B2 | 2/2015 | Lalena |
| 9,282,940 | B2 | 3/2016 | Nishimura |
| 10,335,102 | B2 * | 7/2019 | Lee ............... A61B 6/102 |
| 10,456,100 | B2 | 10/2019 | Ninomiya et al. |
| 2009/0046463 | A1 | 2/2009 | Coombs et al. |
| 2010/0329426 | A1 * | 12/2010 | Oda et al. ............ A61B 6/4405 378/98.2 |
| 2011/0249805 | A1 * | 10/2011 | Kralles et al. ....... A61B 6/4482 378/198 |
| 2011/0249806 | A1 | 10/2011 | Wendlandt et al. |
| 2012/0039447 | A1 | 2/2012 | Lalena et al. |
| 2012/0093298 | A1 | 4/2012 | Lalena |
| 2012/0224673 | A1 | 9/2012 | Barker et al. |
| 2014/0348304 | A1 | 11/2014 | Guldstrand et al. |
| 2016/0021725 | A1 * | 1/2016 | Pellechia ............ G01N 23/083 378/198 |
| 2016/0232691 | A1 | 8/2016 | Nishii et al. |
| 2017/0169648 | A1 | 6/2017 | Penilla et al. |
| 2017/0259729 | A1 | 9/2017 | Balasundrum |

FOREIGN PATENT DOCUMENTS

| | | |
|---|---|---|
| JP | 2014-73310 A | 4/2014 |
| JP | 2015-58342 A | 3/2015 |
| JP | 2016-178992 A | 10/2016 |
| KR | 10-2006-0091506 A | 8/2006 |
| KR | 20-2009-0009461 U | 9/2009 |
| WO | 00/19783 A1 | 4/2000 |
| WO | 2011/130214 A2 | 10/2011 |
| WO | 2016/060614 A1 | 4/2016 |

OTHER PUBLICATIONS

Communication issued by the Korean Intellectual Property Office dated Mar. 20, 2018 in counterpart Korean Patent Application No. 10-2017-0007031.

Communication issued by the European Patent Office dated Feb. 1, 2018 in counterpart European Patent Application No. 17180297.8.

Communication issued by the Korean Intellectual Property Office dated Oct. 16, 2017 in counterpart Korean Patent Application No. 10-2017-0007031.

Communication dated Aug. 26, 2019, issued by the Korean Intellectual Property Office in counterpart Korean Patent Application No. 10-2017-0007031.

Communication dated Aug. 13, 2019, issued by the Korean Intellectual Property Office in counterpart Korean Patent Application No. 10-2017-0007031.

Communication dated Nov. 25, 2019 issued by the Korean Patent Office in counterpart Korean Application No. 10-2017-0007031.

Communication issued by the Korean Intellectual Property Office dated Jun. 5, 2020 in counterpart Korean Patent Application No. 10-2018-0007031.

Communication dated Mar. 12, 2020, issued by the Korean Intellectual Property Office in corresponding Korean Application No. 10-2017-0007031 (Non-Final Rejection).

Communication dated Mar. 12, 2020, issued by the Korean Intellectual Property Office in corresponding Korean Application No. 10-2017-0007031 (Trial Decision).

Communication issued by the European Patent Office dated Dec. 3, 2020, in counterpart European Patent Application No. 17180297.8.

Communication dated Feb. 14, 2022 by the Korean Intellectual Property Office in counterpart Korean Patent Patent application No. 10-2018-0062641.

* cited by examiner

MOBILE X-RAY IMAGING APPARATUS

CROSS-REFERENCE TO RELATED APPLICATION

This application is a continuation of U.S. patent application Ser. No. 15/627,655, filed on Jun. 20, 2017, in the U.S. Patent and Trademark Office, which claims the benefit of Korean Patent Application No. 10-2016-0136249, filed on Oct. 20, 2016, and Korean Patent Application No. 10-2017-0007031, filed on Jan. 16, 2017, in the Korean Intellectual Property Office, the disclosures of which are incorporated herein in their entireties by reference.

BACKGROUND

1. Field

The present disclosure relates to mobile X-ray imaging apparatuses.

2. Description of the Related Art

X-ray imaging apparatuses are used to obtain an image of the inside of an object by using X-rays. X-ray imaging apparatuses may irradiate X-rays towards the object, detect X-rays transmitted through the object, and image the inside of the object in a non-invasive manner. Medical X-ray imaging apparatuses may be used to diagnose an injury or disease of the inside of the object that may not be identified externally.

In a general X-ray imaging apparatus, since an X-ray source and an X-ray detector are fixed to a specific space, a patient needs to visit a test room where the X-ray imaging apparatus is located and position his/her body with respect to the apparatus for X-ray imaging.

However, since patients who have difficulty moving are inconvenienced by X-ray imaging using a general X-ray imaging apparatus, mobile X-ray imaging apparatuses capable of obtaining X-ray images regardless of location have been developed.

A mobile X-ray imaging apparatus having a movable main body is disclosed in which an X-ray source is mounted on the main body. Using a portable X-ray detector in combination with the X-ray source, the mobile X-ray imaging apparatus may provide X-ray imaging for patients having difficulty moving. Even when the mobile X-ray imaging apparatus is used, there may be a limit with respect to a degree of spatial freedom for X-ray imaging according to relative positions of the object and the X-ray imaging apparatus.

SUMMARY

Provided are mobile X-ray imaging apparatuses provided with a column that extends or retracts in a multi-axial direction in which an X-ray source is mounted.

Provided are mobile X-ray imaging apparatuses provided with a display arranged in a column that extends or retracts and displaying an operating state of an X-ray imaging apparatus to a user, an object, and other relevant people.

Provided are mobile X-ray imaging apparatuses in which a blocking member for blocking an annexed apparatus arranged in a column from an external object is arranged.

Provided are mobile X-ray imaging apparatuses including a handler arranged in a column that extends or retracts.

Additional aspects will be set forth in part in the description which follows and, in part, will be apparent from the description, or may be learned by practice of the presented embodiments.

According to an aspect of an embodiment, a mobile X-ray imaging apparatus includes a main body including a driving wheel; a first column rotatably coupled to the main body and extending in one direction; a second column slidably coupled to the first column in an extension direction of the first column; a display provided in the main body and configured to visually display an X-ray irradiation condition; and a visual indicator arranged at one end of the second column and determining a color indicator according to an operating state of the mobile X-ray imaging apparatus, and wherein the visual indicator moves in the extension direction of the first column when the second column slides and moves.

The mobile X-ray imaging apparatus may further include: an X-ray source configured to irradiate an X-ray to an object; and an arm to which the X-ray source is coupled, wherein the arm is coupled to the second column in order to be movable in the extension direction of the first column, and wherein the visual indicator is located higher than the arm in the extension direction of the first column.

The visual indicator may include: a light emitting element; a circuit substrate electrically connected to the light emitting element; a light guide plate configured to uniformly transfer light emitted from the light emitting element; and a controller connected to the circuit substrate and configured to transmit a control signal.

The light emitting element may emit light of various wavelengths.

In a first state in which the second column slides with respect to the first column in a first direction, the visual indicator may be arranged at a height of from about 70 cm to about 150 cm from the ground.

The mobile X-ray imaging apparatus may be movable from a first position to a second position in the first state, and wherein the visual indicator indicates a color indicator that varies according to a moving state and a stop state of the mobile X-ray imaging apparatus.

In a second state in which the second column slides with respect to the first column in a second direction, the visual indicator may be arranged at a height of from about 150 cm to about 230 cm from the ground.

The mobile X-ray imaging apparatus may be fixed to a specific position in the second state, and wherein the visual indicator indicates a color indicator that varies according to an operating state of the X-ray source.

The stop state of the mobile X-ray imaging apparatus may include one of a case where the mobile X-ray imaging apparatus maintains an idle state for a predetermined period of time and a case where a brake for moving the mobile X-ray imaging apparatus is released.

The operating state of the X-ray source may include one of a case where an input signal is input to the X-ray source, the X-ray source is preheated, the X-ray source irradiates an X-ray, and the X-ray source malfunctions.

According to an aspect of another embodiment, a mobile X-ray imaging apparatus includes a main body including a driving wheel; a first column rotatably coupled to the main body and extending in one direction; an X-ray assembly including an X-ray source for irradiating an X-ray to object and an X-ray source support body by which the X-ray source is supported and slidably coupled to the first column in an extension direction of the first column; a display provided in the main body and configured to visually display an X-ray irradiation condition; and a visual indicator arranged on an upper portion of the X-ray assembly and determining a color indicator according to an operating state of the mobile X-ray imaging apparatus, and wherein the visual indicator moves in the extension direction of the first column when the X-ray assembly slides and moves.

The X-ray source support body includes: an arm to which the X-ray source is coupled; and a second column coupled movable to the arm in the extension direction of the first column and slidably coupled to the first column in the extension direction of the first column.

The visual indicator may be located upper than the arm in the extension direction of the first column.

In a first state in which the second column slides with respect to the first column in a first direction, the visual indicator may be arranged at a height of from about 70 cm to about 150 cm from the ground.

The mobile X-ray imaging apparatus may be movable from a first position to a second position in the first state, and wherein the visual indicator indicates a color indicator that varies according to a moving state and a stop state of the mobile X-ray imaging apparatus.

In a second state in which the second column slides with respect to the first column in a second direction, the visual indicator may be arranged at a height of from about 150 cm to about 230 cm from the ground.

The mobile X-ray imaging apparatus may be fixed to a specific position in the second state, and wherein the visual indicator indicates a color indicator that varies according to an operating state of the X-ray source.

The stop state of the mobile X-ray imaging apparatus may include one of a case where the mobile X-ray imaging apparatus maintains an idle state for a predetermined period of time and a case where a brake for moving the mobile X-ray imaging apparatus is released.

In the moving state of the mobile X-ray imaging apparatus, the display may not operate and only the visual indicator operates.

The operating state of the X-ray source may include one of a case where an input signal is input to the X-ray source, the X-ray source is preheated, the X-ray source irradiates an X-ray, and the X-ray source malfunctions.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
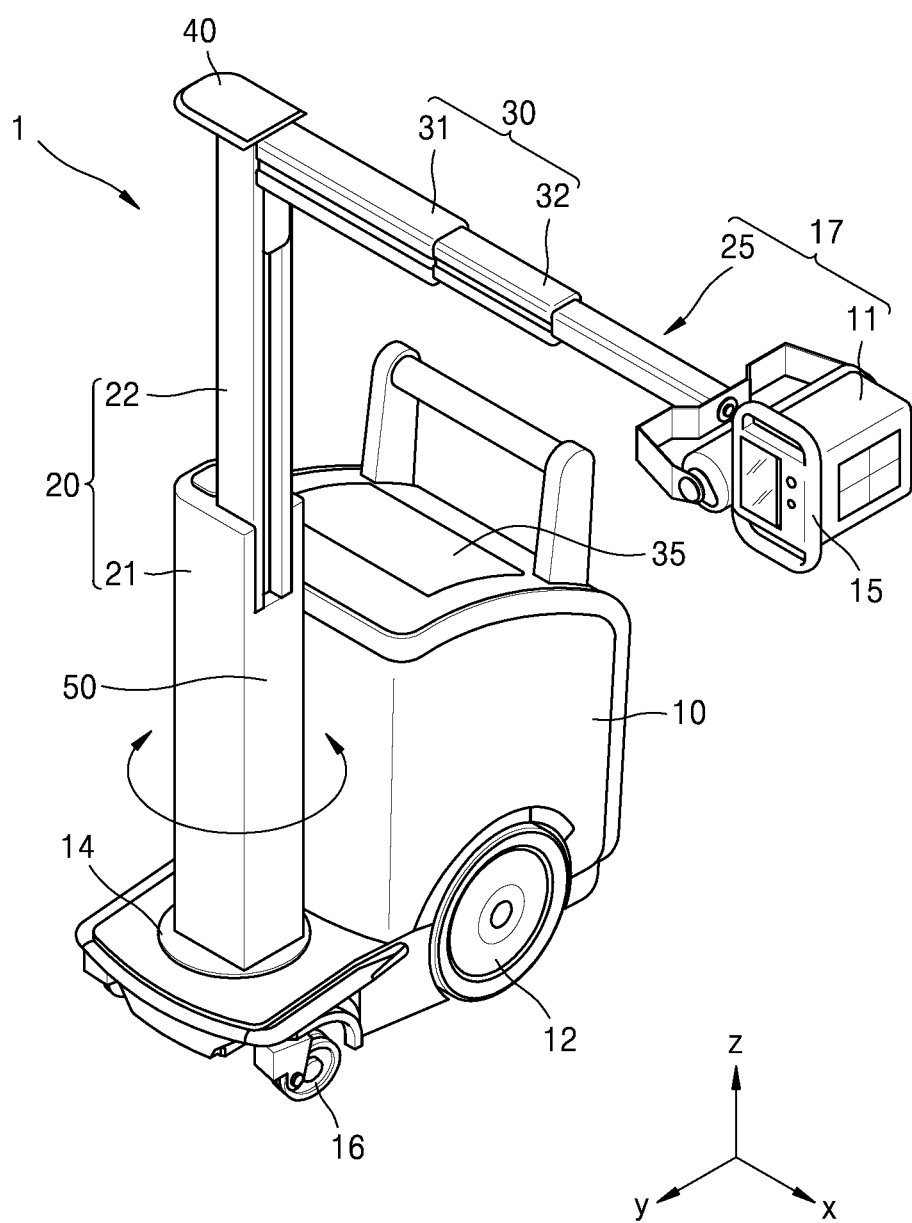
FIG. 1 is a perspective view of a mobile X-ray imaging apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Throughout the specification, an "object" may be a human, an animal, or a part of a human or animal. For example, the object may include an organ (for example, the liver, the heart, the womb, the brain, breasts, or the abdomen), blood vessels, or a combination thereof.

Throughout the specification, a "user" and a "peripheral relevant person" may be, but is not limited to, a medical expert, for example, a medical doctor, a nurse, a medical laboratory technologist, or a medical imaging expert, or a technician who repairs medical apparatuses.

Figure 2:
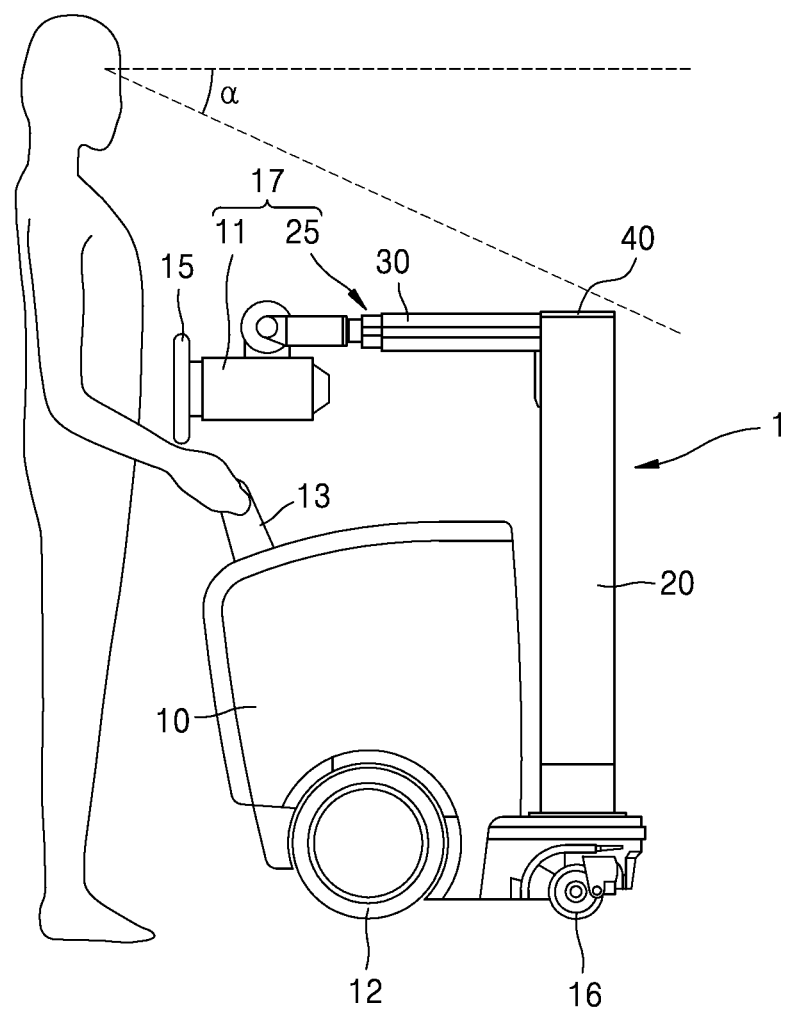
FIG. 2 is a lateral view of a mobile X-ray imaging apparatus according to an embodiment.
Figure 3A:
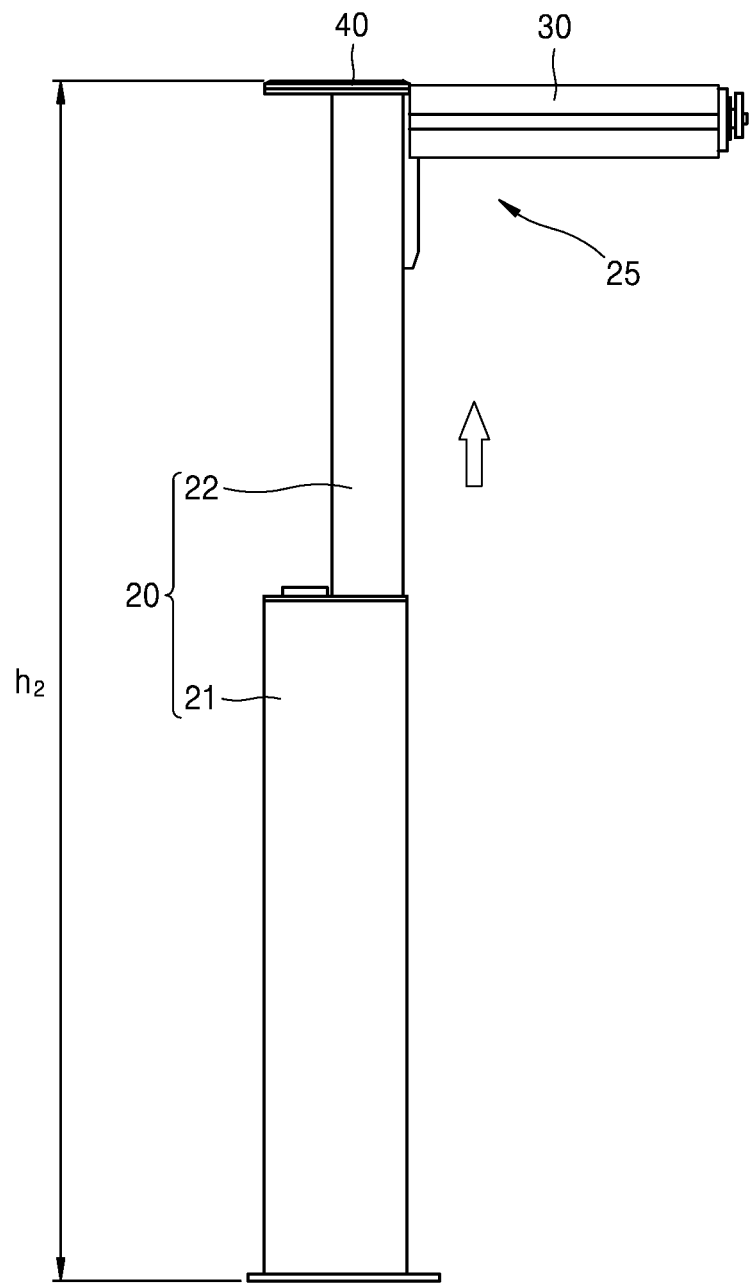
FIGS. 3A and 3B illustrate a column and a indicator of a mobile X-ray imaging apparatus according to an embodiment.
Figure 3B:
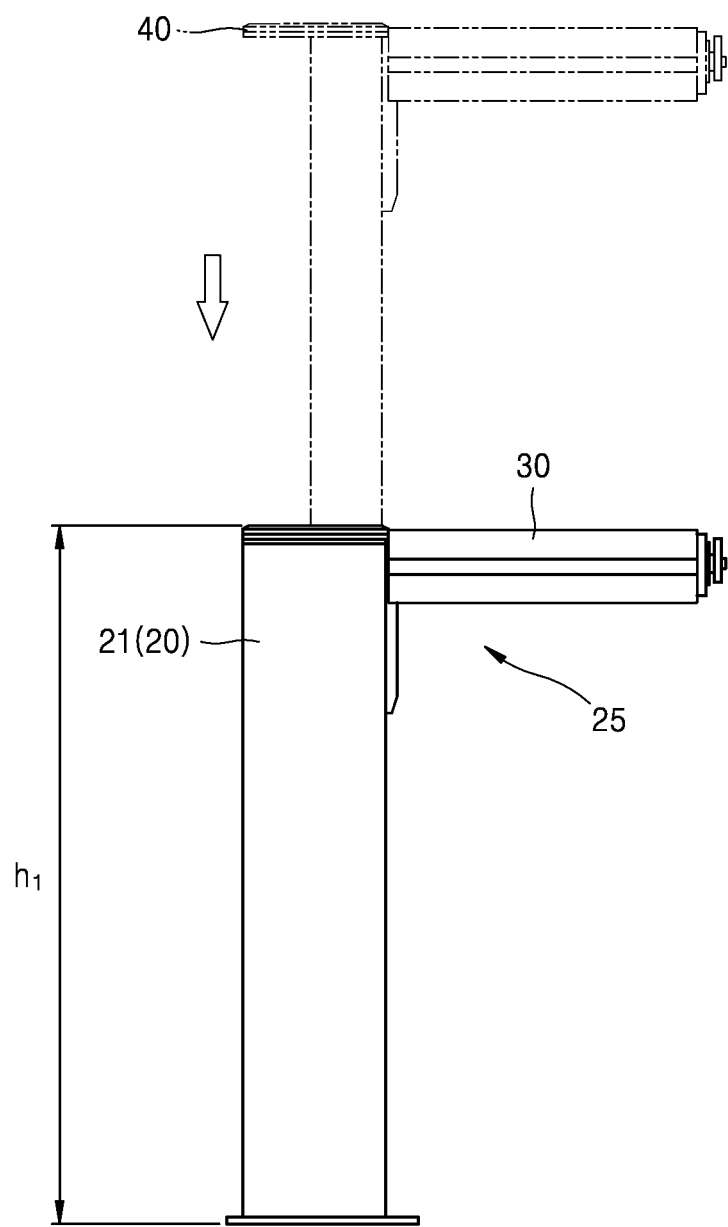

FIG. 1 is a perspective view of a mobile X-ray imaging apparatus 1 according to an embodiment. FIG. 2 is a lateral view of the mobile X-ray imaging apparatus 1 according to an embodiment. FIGS. 3A and 3B illustrate a column and a indicator of a mobile X-ray imaging apparatus according to an embodiment.

Referring to FIGS. 1 through 3B, the mobile X-ray imaging apparatus 1 according to an embodiment may include a main body 10 and an X-ray source 11 mounted in the main body 10. The main body 10 may be movably provided by a driving wheel 12. The main body 10 may be further provided with a caster 16. The caster 16, which is multi-directionally rotatable, may make it easier to change direction when the mobile X-ray imaging apparatus 1 moves.

A handle 13 may be provided in the main body 10 and thus a user may move the main body 10 by holding and pushing or pulling the handle 13. A control panel 15 may be provided in the X-ray source 11. The user may use the control panel 15 to control an operation of the mobile X-ray imaging apparatus 1.

The column 20 having an extending length that may vary may be provided in the main body 10. A rotation panel 14 may be rotatably provided in the main body 10. The column 20 may be mounted in the rotation panel 14. The column 20 may rotate along with the rotation panel 14. As the column 20 rotates, since the X-ray source 11 connected to the column 20 rotates, a position of the X-ray source 11 may vary. As described above, the X-ray source 11 may be provided to have a variable position, and thus X-ray imaging may be performed at various angles.

The column 20 may include a first column 21 and a second column 22 extendable from the first column 21. The second column 22 may be capable of sliding along the first column 21. If the second column 22 slides upward along the first column 21, a length of the column 20 may extend. If the second column 22 slides downward along the first column 21, the length of the column 20 may retract.

An arm 30 having one end to which the X-ray source 11 is coupled may be mounted in the second column 22. The arm 30 may be capable of sliding along the second column 20, and thus a position of the X-ray source 11 may vary in up and down directions.

Also, the mobile X-ray imaging apparatus 1 according to an embodiment may further include a display 35 acting as a display a screen for guiding a user, an X-ray image, a screen for displaying a state of the mobile X-ray apparatus 1 and a visual indicator 40 arranged in one end of the column 20 and displaying imaging related information such as irradiation of X-ray and an operating state of the mobile X-ray imaging apparatus 1 being controlled by a controller 80. A conventional mobile X-ray imaging apparatus includes a sound outputter for outputting a sound output signal and an outputter visually available only to the user, for example, a visual outputter such as a monitor. In this regard, the user identifies an irradiation state of an X-ray by using the visual outputter while an irradiation object of the X-ray and a peripheral relevant person, etc. identify by using, for example, a sound output signal that is output from a sound outputter, rather than a conventional visual outputter. The conventional sound outputter and visual outputter may not readily perform a function of a display apparatus according to an external environment, for example, an existence of an auditory inhibitor such as noise, etc. and a position relationship of the user and the conventional X-ray imaging apparatus.

An X-ray assembly 17 may include an X-ray source 11 for irradiating an X-ray to object and an X-ray source support body 25 by which the X-ray source 11 is supported. In this regard, X-ray source support body 25 according to an embodiment may include the arm 30 and the second column 22. The X-ray assembly 17 may be slidably coupled to the first column 21 in an extension direction of the first column 21. In this regard, a visual indicator 40 may be arranged on an upper portion of the X-ray assembly 17, and thus the visual indicator 40 may move in the extension direction of the first column 21 when the X-ray assembly 17 slides and moves.

Meanwhile, the mobile X-ray imaging apparatus 1 according to an embodiment may include the display 35 to be viewed by the user and the visual indicator 40 that is visually available to the object, the user, and the relevant person as shown in FIG. 1, in addition to the conventional sound outputter (not shown). In this regard, the visual indicator 40 may be arranged at one end of the column 20 as described above so that the visual indicator 40 is directly exposed to an external environment. Also, the visual indicator 40 may be arranged at one end of the column 20 that is movable and may move along with the column 20 in order to adopt to changes in a use environment according to an extension and a retraction of the column 20, and thus the visual indicator 40 may be viewable by the user, the object, and the relevant person at various viewing angles.

For example, as shown in FIG. 2, in a first state in which the user moves the mobile X-ray imaging apparatus 1 from a first position to a second position, a viewing angle α of the user may be fixed toward the front. In this regard, the visual indicator 40 may be arranged at one end of the second column 22 in the retracted column 20, for example, in a state in which the second column 22 is accommodated in the first column 21, as shown in FIG. 3B, and thus the visual indicator 40 may be continuously identified within the viewing angle α of the user. In this regard, a minimum height $h_1$ of the visual indicator 40 may range from about 70 cm to about 150 cm from the ground but the present disclosure is not limited thereto. In this regard, the ground refers to a support surface by which a lowest part of the mobile X-ray imaging apparatus 1 is supported, for example, a floor surface of a building in which the mobile X-ray imaging apparatus 1 is moving or a floor surface of an X-ray imaging room in which X-ray imaging is performed. Thus, the user may not only determine an operating state of the mobile X-ray imaging apparatus 1 without viewing the display 35 while moving but also determine a malfunction of the mobile X-ray imaging apparatus 1 immediately when the malfunction occurs.

Also, as shown in FIG. 3A, in a second state in which the mobile X-ray imaging apparatus 1 is fixed to a specific position in order to use the mobile X-ray imaging apparatus 1, i.e. when the column 20 extends in order to use the mobile X-ray imaging apparatus 1, for example, when the second column 22 slides from the first column 21 and is exposed to outside, the visual indicator 40 arranged in one end of the second column 22 may be arranged in a highest position of the mobile X-ray imaging apparatus 1. In this regard, the visual indicator 40 may be arranged in a position higher than that of the arm 30 to which the X-ray source 11 is coupled. Also, a maximum height $h_2$ of the visual indicator 40 may be determined in consideration of heights of the user, the object, and the relevant person and a height of the peripheral inhibitor. For example, the maximum height $h_2$ of the visual indicator 40 may range from about 150 cm to about 230 cm but the present disclosure is not limited thereto. As described above, the visual indicator 40 may be arranged in a higher position than general viewing angles of the user, the object, and the relevant person, and thus visibility of the user, the object, and the relevant person with respect to the visual indicator 40 may be improved. That is, the user, the object, and the relevant person may visually identify the visual indicator 40 irrespective of relative positions of the mobile X-ray imaging apparatus 1, the user, the object, the relevant person, and the peripheral inhibitor. Thus, the user, the object, and the relevant person may identify the operating state of the mobile X-ray imaging apparatus 1 in real time in a peripheral environment, for example, noise or a confusing situation such as an emergency room.

Also, the visual indicator 40 according to an embodiment may display various operating states of the mobile X-ray imaging apparatus 1 according to a display method. For example, the visual indicator 40 may display various operating states of the mobile X-ray imaging apparatus 1 by using a visual indicator, for example, text, images, or a change of colors. Thus, compared to a case where various operating states of the mobile X-ray imaging apparatus 1 are displayed by using a conventional auditory indicator, irrespective of an auditory eternal factor, for example, an auditory inhibitor that occurs in an emergency environment in which the mobile X-ray imaging apparatus 1 may be used, the user, the object, and the relevant person may identify the operating state of the mobile X-ray imaging apparatus 1. In addition, the visual indicator 40 may use the visual indicator, and thus the user, the object, and the relevant person may identify the operating state of the mobile X-ray imaging apparatus 1 in real time. However, the present disclosure is not limited thereto. A visually displayed indicator may be used in the visual indicator 40. The visual indicator 40 that uses a change of colors as the visual indicator will be described in more detail below.

Figure 4:
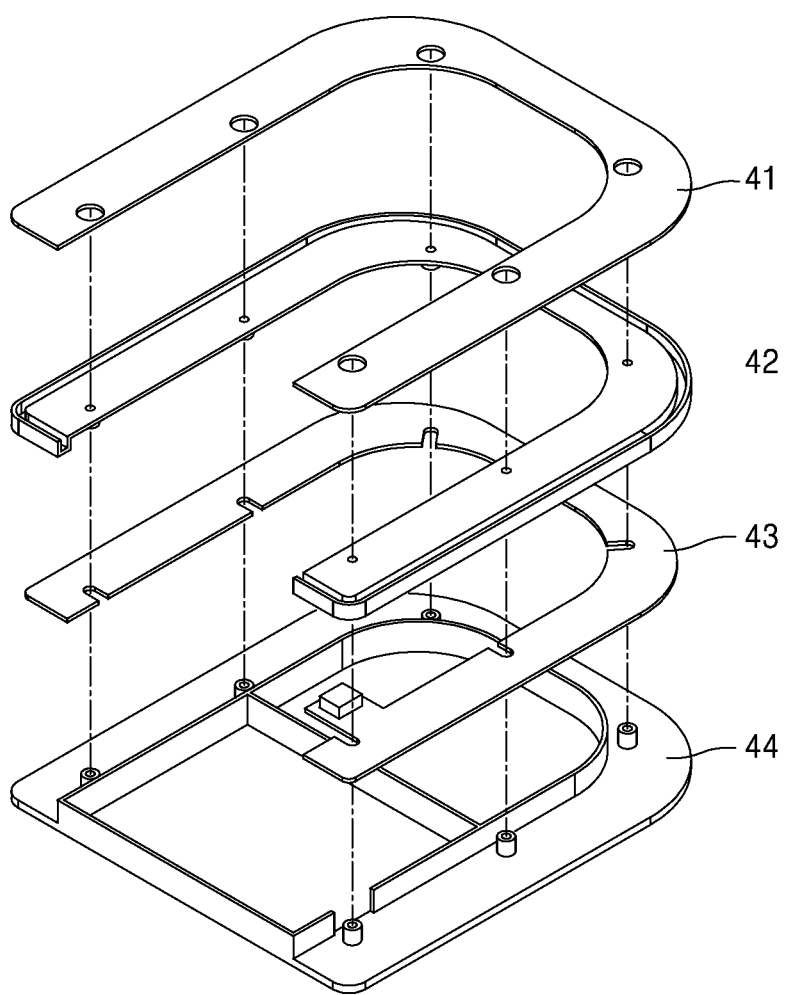
FIG. 4 is an exploded perspective view of a indicator according to an embodiment.
Figure 5:
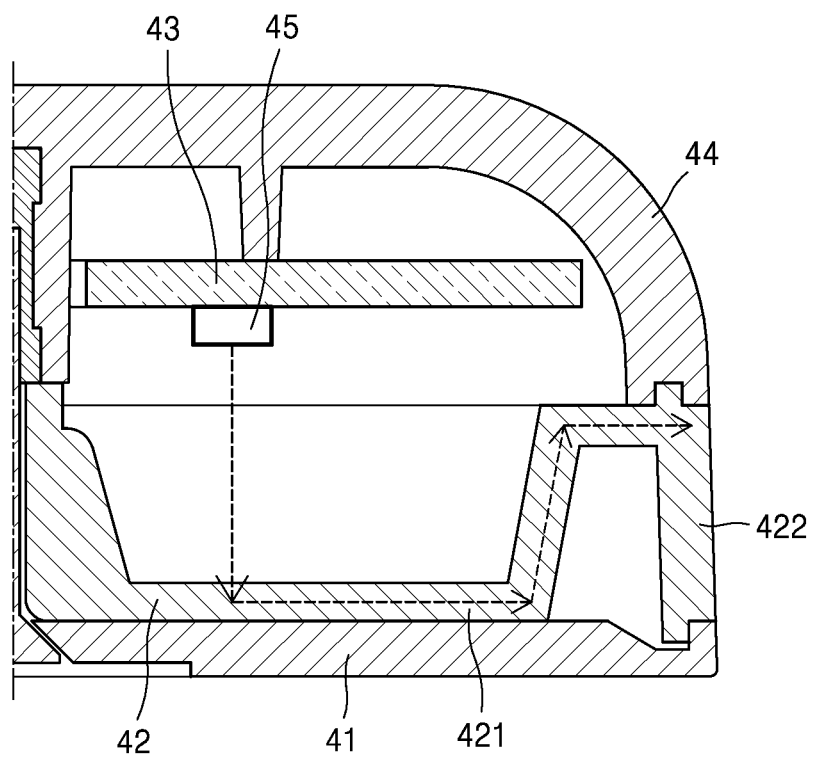
FIG. 5 is a cross-sectional view of a indicator according to an embodiment.

FIG. 4 is an exploded perspective view of the visual indicator 40 according to an embodiment. FIG. 5 is a cross-sectional view of the visual indicator 40 according to an embodiment.

Referring to FIGS. 4 and 5, the visual indicator 40 according to an embodiment may include a first case 41 and a second case 44 that may be coupled to each other, a circuit substrate 43 that may include a light emitting element 45, and a outputter 42 that receives light from the light emitting element 45 and displays the light to outside.

As an example, the first case 41 may be an accommodation apparatus extending in a '☐' shape, and the second case 42 may be provided in correspondence to the first case 41 and coupled to the first case 41 so that the first case 41 and the second case 42 may form an accommodation space in which the outputter 42 and the circuit substrate 43 are accommodated.

The circuit substrate 43 may be a substrate apparatus in which the light emitting element 45 is arranged and may be provided as, for example, a printed circuit board (PCB) but the present disclosure is not limited thereto. The circuit substrate 43 may be provided in the '☐' shape in correspondence to the first case 41. In this regard, the light emitting element 45 may be provided as one or more elements that may be spaced apart from each other by a predetermined gap in an extension direction of the circuit substrate 43. For example, the light emitting element 45 may be an LED element with various colors but the present disclosure is not limited thereto. The circuit substrate 43 may be connected to the controller 80 that will be described later, and accordingly, whether the light emitting element 45 emits light may be controlled.

The outputter 42 may be a display apparatus for displaying light emitted from the light emitting element 45 to outside. As an example, the outputter 42 may be provided as a light guide plate to uniformly transfer light to outside. For example, the outputter 42 may include a panel 421 arranged to face the light emitting element 45 and an exposure unit 422 connected to the panel 421 and having one surface exposed to outside. As an example, the panel 421 and the exposure unit 422 may include transparent acryl, thereby performing a function of uniformly scattering light emitted from the light emitting element 45 over an entire region of the exposure unit 422. Accordingly, the user, the object, and the relevant person may visually recognize light of various colors emitted from the outputter 42 and identify the operating state of the mobile X-ray imaging apparatus 1. An example of an operating state of the visual indicator 40 according to the operating state of the mobile X-ray imaging apparatus 1 will be described below.

Figure 6:
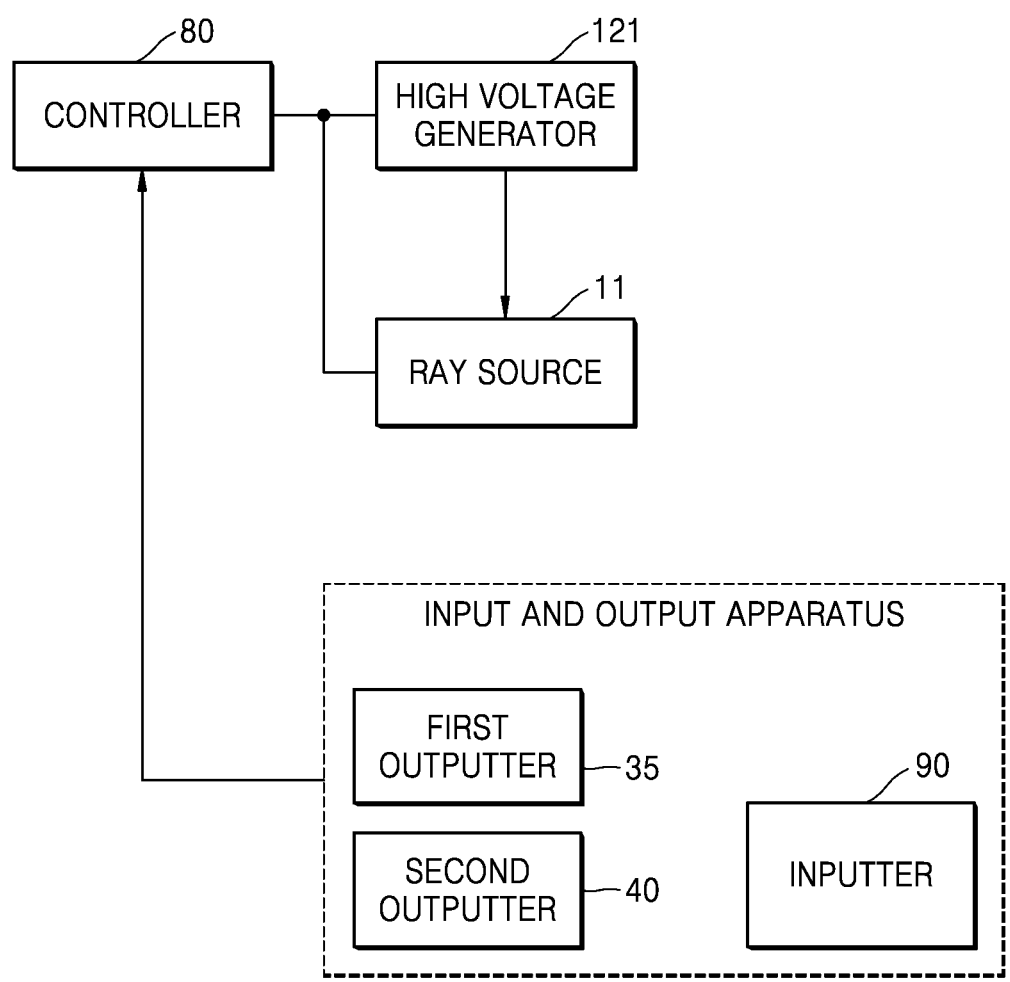
FIG. 6 is a block diagram of a mobile X-ray imaging apparatus according to an embodiment.

FIG. 6 is a block diagram of the mobile X-ray imaging apparatus 1 according to an embodiment.

The mobile X-ray imaging apparatus 1 according to an embodiment may further include the controller 80 for controlling an operation of the mobile X-ray imaging apparatus 1 and an inputter 90 for inputting a control command, in addition to the display 35 and indicators 40 that display an operating state of the mobile X-ray imaging apparatus 1. The inputter 90 may include a keyboard, a mouse, a touch screen, a voice recognizer, a fingerprint recognizer, an iris recognizer, etc. and may include other input apparatuses that are obvious to one of ordinary skill in the art. A user may input a command for irradiation of X-rays through the inputter 90. A switch for inputting the command may be provided in the inputter 90.

As an example, when the mobile X-ray imaging apparatus 1 is not used or the mobile X-ray imaging apparatus 1 is moved as shown in FIG. 2, the outputter 42 of the visual indicator 40 may display a first indicator, for example, a blue indicator. In this regard, the display 35 may not operate, and accordingly, the user, an object, and a relevant person may identify the visual indicator 40 to determine a use state of the mobile X-ray imaging apparatus 1.

Next, the user may input the command for irradiation of X-rays through the inputter 90. As an example, the user may input the command for irradiation of X-rays by pressing the switch provided in the inputter 90 twice. As an example, when the user presses the switch provided in the inputter 90 once, a preparation command for instructing preheating for irradiation of X-rays may be input to the switch. In this regard, the controller 80 may control the visual indicator 40 to display a second indicator, for example, a bright green indicator, on the outputter 42.

Next, when the user presses the switch provided in the inputter 90 once more, an irradiation command for substantial irradiation of X-rays may be input to the switch. In this case, a high voltage generator 121 that generates high voltage for generating X-rays may start preheating, and, if preheating is prepared, output a preparation complete signal to the controller 80. In this regard, the controller 80 may control the visual indicator 40 to display a third indicator, for example, a green indicator, on the outputter 42.

Next, if preheating of the high voltage generator 121 is complete, and an irradiation signal from the inputter 90 to the high voltage generator 121 is output, the high voltage generator 121 may generate high voltage and apply the high voltage to the X-ray source 11. The X-ray source 11 may irradiate X-rays. In this regard, the controller 80 may control the visual indicator 40 to display a fourth indicator, for example, a yellow indicator, on the outputter 42.

Next, since the mobile X-ray imaging apparatus 1 malfunctions, when an emergency button is pressed by the user or a malfunction state is recognized by the controller 80, the controller 80 may control the visual indicator 40 to display a fifth indicator, for example, a red flickering indicator, on the outputter 42.

In addition, the visual indicator 40 according to an embodiment may display a moving state of the mobile X-ray imaging apparatus. According to an embodiment, when a brake (not shown) of the mobile X-ray imaging apparatus 1 is released by the user, the controller 80 may control the visual indicator 40 to display a sixth indicator, for example, a white indicator, on the outputter 42.

Next, when the brake (not shown) of the mobile X-ray imaging apparatus 1 is released, and an external force is input by the user or an input signal for moving the mobile X-ray imaging apparatus 1 is input to the inputter 90, the controller 80 may control the visual indicator 40 to display a seventh indicator, for example, a blue flickering indicator, on the outputter 42.

Next, when the mobile X-ray imaging apparatus 1 does not operate for a predetermined period of time and maintains an idle state, the controller 80 may control the visual indicator 40 to display an eighth indicator, for example, a white flickering indicator, on the outputter 42. As described above, specific color displays may correspond to various operating states of the mobile X-ray imaging apparatus 1 one by one, and specific color indicators may be output from the visual indicator 40 according to various operating states of the mobile X-ray imaging apparatus 1, and thus the user, the object, and the relevant person may identify and prepare for various operating states of the mobile X-ray imaging apparatus 1 in real time.

Figure 7A:
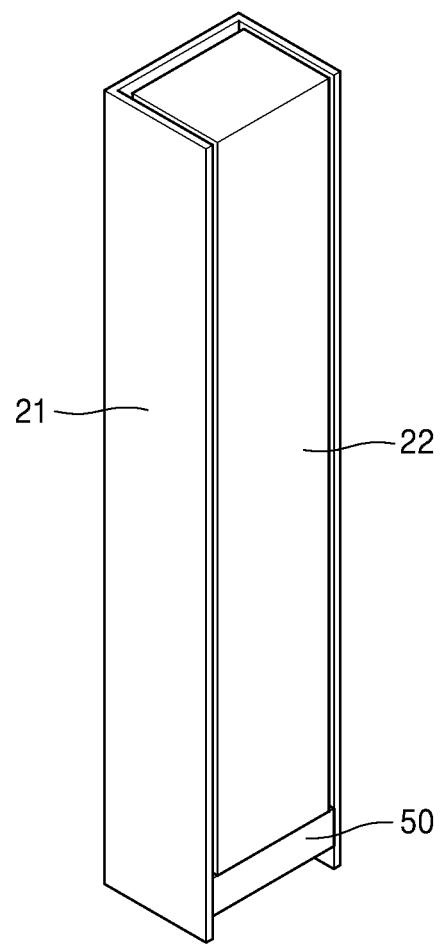
FIGS. 7A through 7C illustrate a column and a blocker of a mobile X-ray imaging apparatus according to an embodiment.
Figure 7B:
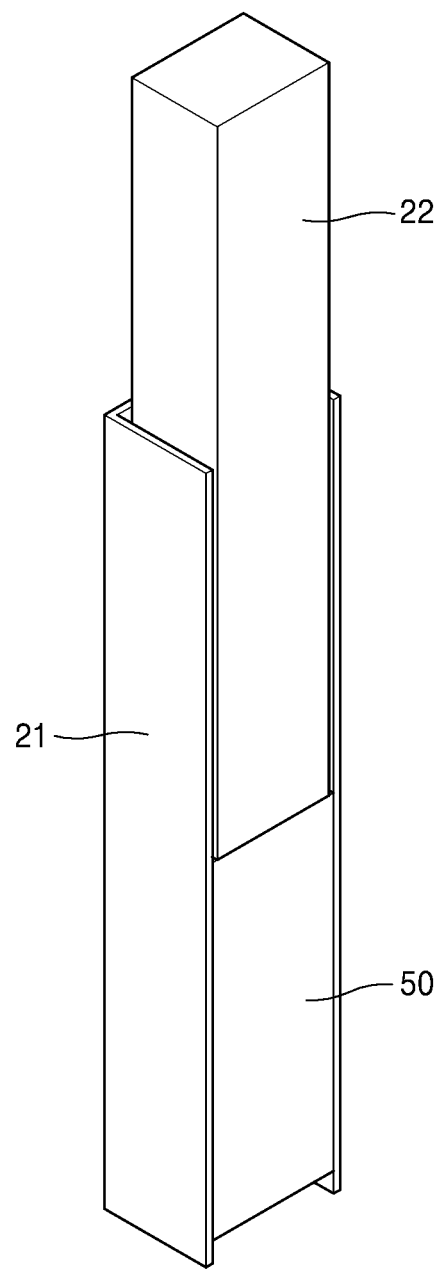
Figure 7C:
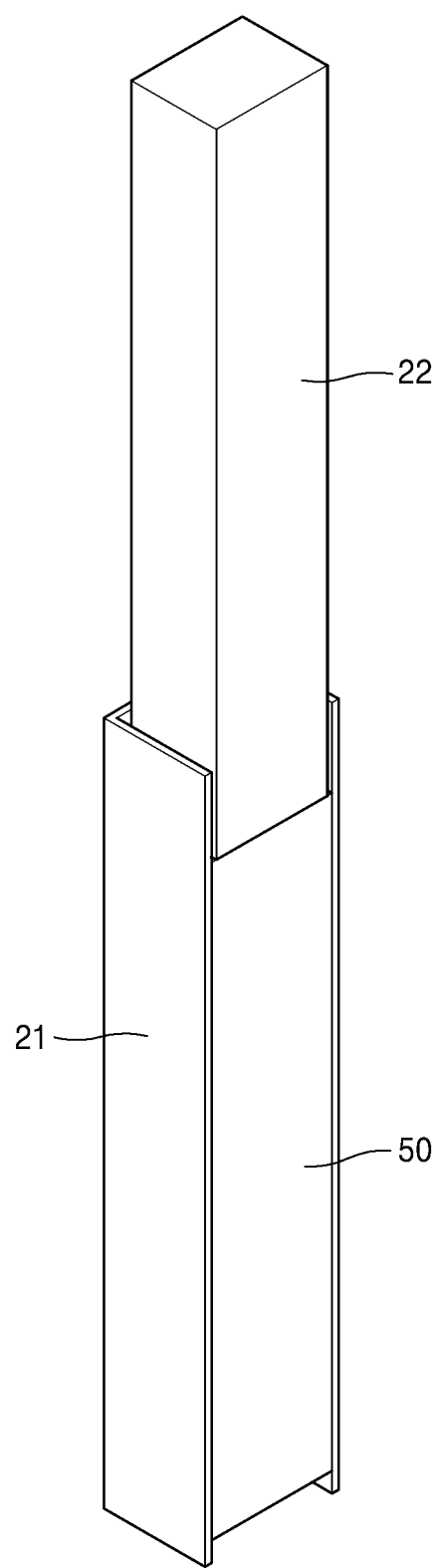
Figure 8A:
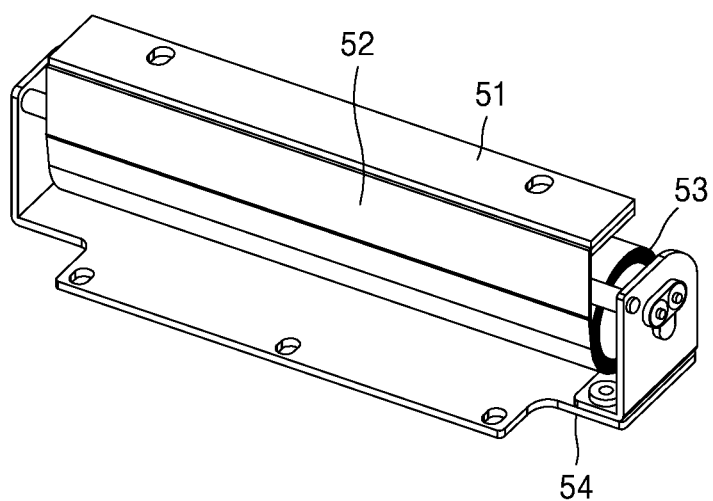
FIG. 8A is a perspective view of a blocker according to an embodiment.
Figure 8B:
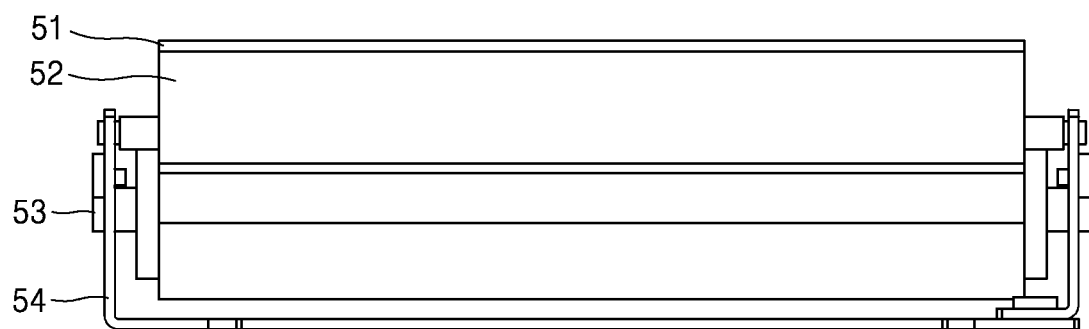
FIG. 8B is a lateral view of a blocker according to an embodiment.
Figure 8C:
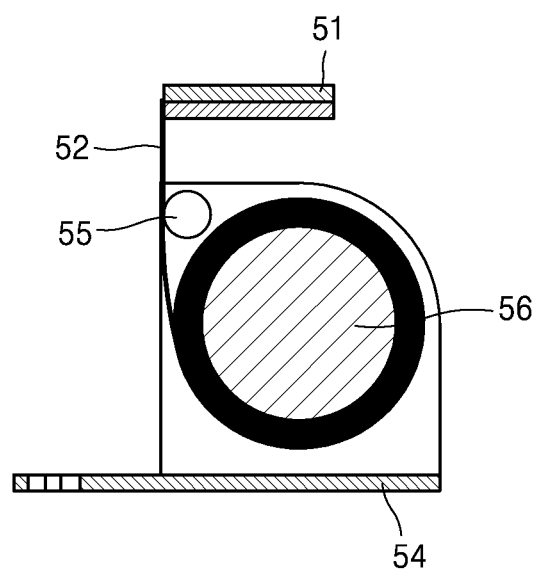
FIG. 8C is a front view of a blocker according to an embodiment.

FIGS. 7A through 7C illustrate the column 20 and a blocker 50 according to an embodiment. FIG. 8A is a perspective view of the blocker 50 according to an embodiment. FIG. 8B is a lateral view of the blocker 50 according to an embodiment. FIG. 8C is a front view of the blocker 50 according to an embodiment.

Referring to FIGS. 7A through 8C, the X-ray imaging apparatus according to an embodiment may not include a separate driving source and may manually extend or retract a length of the column 20. A structure of the column 20 with a manually increasing or reducing length will be described below.

The column 20 according to an embodiment may include a first column 21, a second column 22, and the blocker 50 movable in connection with the second column 22. For example, the first column 21 may be a fixing member, and the second column 22 may be an extension and reduction member that is slidably arranged in the first column 21. A moving direction of the second column 22 may be regulated by a slide arranged in a side part of the second column 22 and a slide guide provided in the first column 21.

The blocker 50 according to an embodiment may include a support member 51 fixed to a lower portion of the second column 22, a blind member 52 having one end fixed to the support member 51 and another end fixed to one part of a roller 53, the roller 53 for winding the blind member 52, and a case 54 for supporting the roller 53.

The support member 51 according to an embodiment may be provided in a rod shape extending in one direction and may have one surface fixed to a lower part of the second column 22. In this regard, the blind member 52 that will be described later may be fixed to another surface of the support member 51. One surface of the support member 51 may be fixed to the lower part of the second column 22 and the blind member 52 that will be described later may be fixed to another surface of the support member 51, and thus the support member 51 may move up and down in connection with a movement of the second column 22, and one end of the blind member 52 may move up and down according to the movement of the support member 51.

The blind member 52 may be a blocking member provided in the form of a flexible material that may be wound by the roller 53. For example, the blind member 52 may be provided as a flexible and elastic member. In this regard, the blind member 52 may be provided in an opaque material but the present disclosure is not limited thereto. One end of the blind member 52 may be fixed to the support member 51, and another end thereof may be fixed to the roller 53. Accordingly, as described above, when the second column 22 moves up and down, the support member 51 may also move up and down in connection with the second column 22. In this regard, the blind member 52 having one end fixed to the support member 51 may also move up and down in connection with the movement of the support member 51.

For example, when the second column 22 moves up, the support member 51 may also move up in connection with the second column 22. In this regard, the blind member 52 having one end fixed to the support member 51 may also move up in connection with the movement of the support member 51. In this regard, the roller 53 may rotate in one direction, and thus the blind member 52 wounded by the roller 53 may also be unwounded and may move up along a movement direction of the support member 51. In this regard, a regulator 55 for regulating a shape of the blind member 52 and provided in a roller shape may be arranged in a travel section of the blind member 52, thereby regulating the shape such that the blind member 52 may move up in a flat shape. For example, when an up movement of the second column 22 is complete, the support member 51 fixed to the second column 22 may act as a stopper, and accordingly, the roller 22 may stop rotating in another direction, and the blind member 52 may also stop unwinding.

Also, for example, when the second column 22 moves down, the support member 51 may also move down in connection with the second column 22. In this regard, the blind member 52 having one end fixed to the support member 51 may also move down in connection with the movement of the support member 51. In this regard, an elastic member 56 that may apply a torque to the roller 22 in another direction, for example, a leaf spring, may be arranged in the roller 53. Accordingly, the roller 22 may rotate in one direction in another direction, and thus a predetermined tension may be applied to the blind member 52 such that the blind member 52 may be wounded again by the roller 53. For example, when a down movement of the second column 22 is complete, the support member 51 fixed to the second column 22 may act as a stopper, and accordingly, the roller 22 may stop rotating in another direction, and the blind member 52 may also stop rewinding.

As described above, since the blind member 52 may also move up in connection with the up and down movements of the second column 22, when the second column 22 retracts, a front part of the first column 21 that is a movement path in which the second column 22 extends or retracts may not be exposed to outside by the second column 22, and when the second column 22 extends, the front part may not be exposed to outside by the blind member 52. Thus, a high voltage member arranged in the first column 21 may prevent a risk exposed to the user, the object, and the relevant person as well as may prevent a malfunction that a movement path of the second column 22 is blocked due to impurities inserted into the first column 21.

Figure 9A:
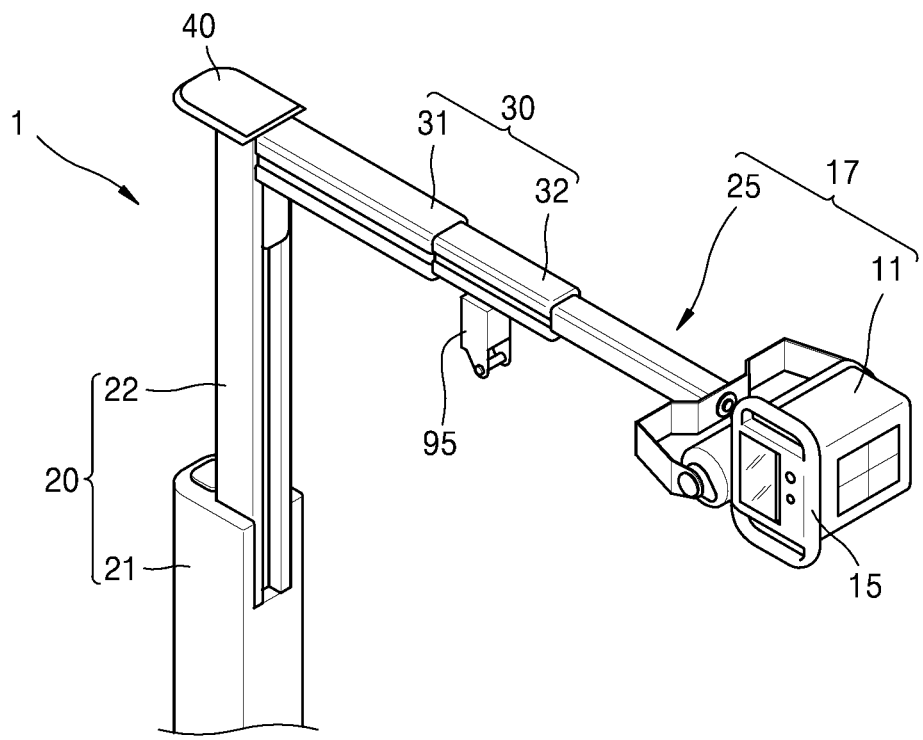
FIGS. 9A and 9B are partial perspective views of an arm according to an embodiment.
Figure 9B:
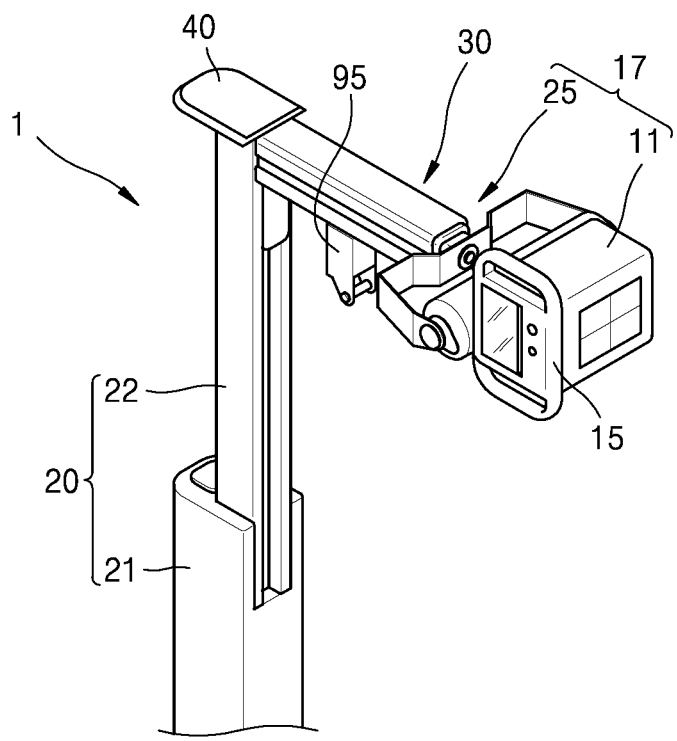

FIGS. 9A and 9B are partial perspective views of an arm 30 according to an embodiment.

Referring to FIGS. 1, 9A, and 9B, the arm 30 according to an embodiment may be extendable. The arm 30 may extend or retract, and thus the X-ray source 11 mounted in an end of the arm 30 may move in a side direction such that a position of the X-ray source 11 may vary.

For example, the arm 30 may include a first arm 31 that is slidable along the second column 22 and a second arm 32 that is extendable from the first arm 31. The X-ray source 11 may be mounted in an end of the second arm 32. The second arm 32 may slide from the first arm 31 in one direction or in another direction, and thus a length of the arm 30 may extend or retract. A configuration of the arm 30 is not limited to described above.

When the mobile X-ray imaging apparatus 1 is moved by a user, lengths of the column 20 and the arm 30 may retract in order to secure viewing of the user and prevent collision with an obstacle. The second column 22 may be located to overlap with the first column 21. The second arm 22 may be located to overlap with the first arm 21. Thus, the lengths of the column 20 and the arm 30 may be minimized. The X-ray source 11 mounted in the arm 30 may be located in an upper portion of the main body 10 in order to avoid a shock with an external obstacle.

When the mobile X-ray imaging apparatus 1 moves, the lengths of the column 20 and the arm 30 may retract in order to safely move the mobile X-ray imaging apparatus 1. When X-ray is imaged by the mobile X-ray imaging apparatus 1, the lengths of the column 20 and the arm 30 may increase by varying a position of the X-ray source 11 in order to facilitate X-ray imaging.

Also, an object may be arranged in a lower portion of the X-ray source 11, and the user is located between the main body 10 and the object, the user may be difficult to directly manipulate a holder provided in the X-ray source 11 in order to adjust a position of the X-ray source 11. In this regard, a handler 95 that may be held by the user may be provided in the second arm 32. In this regard, the handler 95 may be fixed to the second arm 32, and accordingly, the handler 95 may also move in connection with a movement of the second arm 32. Thus, the user may move the second arm 32 while holding the handler 95, thereby more easily adjusting a relative position of the X-ray source 11 irrespective of a position of the object.

A mobile X-ray imaging apparatus according to an embodiment may adjust a position of an X-ray source in various ways, thereby performing X-ray imaging at various angles and ranges. Also, an operating process of the mobile X-ray imaging apparatus may be transferred to a user, an object, and a relevant person in real time. Also, the mobile X-ray imaging apparatus may prevent external impurities from being inserted into a column that extends or retracts and protect the user, the object, and the relevant person from a high voltage wire, etc. arranged in the extended or retracted column. Also, the user may easily extend or retract the X-ray source between the objet and a main body of the mobile X-ray imaging apparatus.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A mobile X-ray imaging apparatus comprising:
    a main body comprising a driving wheel;
    a column rotatably coupled to the main body and extending in one direction;
    an X-ray source connected to the column;
    a visual indicator that is attached to one end of the column, and
    a controller controlling an operating state of the mobile X-ray imaging apparatus,
    wherein the controller is configured to control the visual indicator to change color of the visual indicator into a first color based on receiving an input signal indicating that preheating for radiation of X-ray is started and into a second color based on receiving an input signal for moving the mobile X-ray imaging apparatus.

2. The mobile X-ray imaging apparatus of claim 1, wherein the color of the visual indicator is changed to a third color, based on receiving a signal indicating that an idle state of the mobile X-ray imaging apparatus is started, and the visual indicator displays the third color during the idle state of the mobile X-ray imaging apparatus.

3. The mobile X-ray imaging apparatus of claim 1, wherein the visual indicator emits light through at least three surfaces exposed to an outside of the mobile X-ray imaging apparatus.

4. The mobile X-ray imaging apparatus of claim 3, wherein the visual indicator comprises:
    a light emitting element;
    a circuit substrate electrically connected to the light emitting element; and
    a light guide plate uniformly scattering the light emitted from the light emitting element over the at least three surfaces;
    wherein the controller is connected to the circuit substrate and configured to transmit a control signal.

5. The mobile X-ray imaging apparatus of claim 1, wherein the column comprises:
    a first column rotatably coupled to the main body and extending in an extension direction that corresponds to the direction in which the column is extending; and
    a second column slidably coupled to the first column in the extension direction of the first column.

6. The mobile X-ray imaging apparatus of claim 5, wherein the visual indicator is located above an arm in the extension direction of the first column.

7. The mobile X-ray imaging apparatus of claim 5, wherein the first column is coupled to the main body and extends in an upward direction and the second column is accommodated in the first column and configured to be slidable with respect to the first column in the upward direction,
    wherein the first column has one side surface to expose one surface of the second column accommodated in the first column from outside, and
    wherein the mobile X-ray imaging apparatus further comprising:
    a blocker comprising a blind member having a first end that is coupled to the first column, and a second end coupled to the second column and configured to move in the upward direction when the second column slides up in the upward direction, and the blocker being configured to block the one side surface of the first column from outside as the second column slides up in the upward direction.

8. The mobile X-ray imaging apparatus of claim 7, wherein the blocker comprises,
    a support member connected between the second column and the blind member;
    a roller winding the blind member; and
    a case fixed to the first column and supporting the roller,
    wherein the blind member connected to the support member extends as the support member slides up in the upward direction.

9. The mobile X-ray imaging apparatus of claim 8, wherein the blocker further comprises a shape regulator arranged in an extension path of the blind member and configured to regulate a shape of the blind member.

10. The mobile X-ray imaging apparatus of claim 8, further comprising:
    an elastic member configured to apply a torque to the roller when the blocker moves and the blind member winds.

11. A mobile X-ray imaging apparatus comprising:
    a main body comprising a driving wheel;
    a column rotatably coupled to the main body and extending in one direction;
    an X-ray source connected to the column; and
    a visual indicator that is attached to one end of the column,
    wherein the visual indicator is configured to change a color based on receiving a signal indicating that preheating for radiation of X-ray is started, and display the color during the preheating for radiation of the X-ray, and
    wherein the visual indicator comprises an U-shaped outputter that is configured to emit light to an outside of the U-shaped outputter via a surface exposed to the outside of the U-shaped outputter.

12. A mobile X-ray imaging apparatus comprising:
    a main body comprising a driving wheel;

a column rotatably coupled to the main body and extending in one direction, and comprising a first column rotatably coupled to the main body and extending in one direction;

and a second column slidably coupled to the first column in the extension direction of the first column;

an X-ray source connected to the column; and a blocker comprising a blind member having a first end and a second end, wherein the first end of the blind member is disposed at a fixed state and when the second end of the blind member moves away from the first end in a direction in which the second column slides up, the blind member of the blocker extends in the direction in which the second column slides up and blocks a space formed inside the first column from outside.

13. The mobile X-ray imaging apparatus of claim 12, further comprising:

a visual indicator that is attached to one end of the column and that is configured to change in color, wherein based on receiving a signal indicating that a state of the mobile X-ray imaging apparatus changes from a stop state to a moving state, the visual indicator changes to a first color, wherein the color of the visual indicator is changed to a second color, based on receiving a signal indicating that an idle state of the mobile X-ray imaging apparatus is started, and the visual indicator displays the second color during the idle state of the mobile X-ray imaging apparatus.

14. The mobile X-ray imaging apparatus of claim 13, wherein the visual indicator is further configured to have a horizontally aligned U-shape and horizontally emits light to an outside of the horizontally aligned U-shape via an entire surface exposed to the outside of the horizontally aligned U-shape.

15. The mobile X-ray imaging apparatus of claim 12, further comprising:

an arm extending in another direction and connecting the column to the X-ray source; and a visual indicator located above the arm in the extension direction of the first column.

16. The mobile X-ray imaging apparatus of claim 12, wherein the blocker comprises, a support member connected between the second column and the blind member;

a roller winding the blind member; and a case fixed to the first column and supporting the roller wherein the blind member connected to the support member extends as the support member slides up in an upward direction.

17. The mobile X-ray imaging apparatus of claim 16, wherein the blocker further comprises a shape regulator arranged in an extension path of the blind member and configured to regulate a shape of the blind member.

18. The mobile X-ray imaging apparatus of claim 16, further comprising:

an elastic member configured to apply a torque to the roller when the blocker moves and the blind member winds.

19. The mobile X-ray imaging apparatus of claim 12, wherein the second column is coupled to the second end of the blind member.

* * * * *